(12) United States Patent
Xu et al.

(10) Patent No.: US 12,211,204 B2
(45) Date of Patent: Jan. 28, 2025

(54) AI DRIVEN LONGITUDINAL LIVER FOCAL LESION ANALYSIS

(71) Applicant: SIEMENS HEALTHINEERS AG, Forchheim (DE)

(72) Inventors: Zhoubing Xu, Plainsboro, NJ (US); Guillaume Chabin, Paris (FR); Matteo Barbieri, Paris (FR); Alin Madalin Draghia, Brasov (RO); Manasi Datar, Mumbai (IN); Thomas Pheiffer, Philadelphia, PA (US); Ioan Marius Popdan, Brasov (RO); Robert Grimm, Nuremberg (DE); Heinrich von Busch, Uttenreuth (DE); Sasa Grbic, Plainsboro, NJ (US)

(73) Assignee: Siemens Healthineers AG, Forchheim (DE)

(*) Notice: Subject to any disclaimer, the term of this patent is extended or adjusted under 35 U.S.C. 154(b) by 388 days.

(21) Appl. No.: 17/648,940

(22) Filed: Jan. 26, 2022

(65) Prior Publication Data

US 2023/0237647 A1   Jul. 27, 2023

(51) Int. Cl.
| | | |
|---|---|---|
| G06T 7/00 | (2017.01) | |
| G06T 7/10 | (2017.01) | |
| G06T 7/30 | (2017.01) | |
| G06T 7/62 | (2017.01) | |
| A61B 6/00 | (2006.01) | |

(52) U.S. Cl.
CPC .............. *G06T 7/0012* (2013.01); *G06T 7/10* (2017.01); *G06T 7/30* (2017.01); *G06T 7/62* (2017.01);

(Continued)

(58) Field of Classification Search
CPC ........... G06T 7/0012; G06T 7/30; G06T 7/62; G06T 7/10; G06T 7/00;
(Continued)

(56) References Cited

U.S. PATENT DOCUMENTS

| | | | | |
|---|---|---|---|---|
| 11,587,236 B2* | 2/2023 | Palma | ................... | G16H 30/40 |
| 2009/0041322 A1* | 2/2009 | Wolf | ..................... | G06T 7/0012 |
| | | | | 382/131 |

OTHER PUBLICATIONS

Elsinger et al., "LI-RADS, Liver Imaging Reporting and Data System", retrieved at https://radiologyassistant.nl/abdomen/liver/li-rads, 2020, 46 pgs.
(Continued)

*Primary Examiner* — Tuan H Nguyen

(57) ABSTRACT

Systems and methods for performing an assessment of a lesion are provided. A plurality of input medical images of a lesion is received. The plurality of input medical images comprises an initial input medical image and one or more additional input medical images. The initial input medical image comprises a region of interest around the lesion. A mask of the lesion is curated for the initial input medical image based on the region of interest and a set of candidate masks. The region of interest in the initial input medical image is propagated to the one or more additional input medical images based on prior registration transformations. A mask of the lesion is curated for each of the one or more additional input medical images based on the propagated regions of interest and the set of candidate masks. One or more assessments of the lesion are performed based on the mask for the initial input medical image, the masks for the one or more additional input medical images, and prior assessments of lesions. Results of the one or more assessments of the lesion are output.

20 Claims, 8 Drawing Sheets

(52) U.S. Cl.
CPC ... *A61B 6/5217* (2013.01); *G06T 2207/20084* (2013.01); *G06T 2207/20104* (2013.01); *G06T 2207/30096* (2013.01)

(58) Field of Classification Search
CPC . G06T 2207/30096; G06T 2207/20084; G06T 2207/20104; A61B 6/5217
See application file for complete search history.

(56) References Cited

OTHER PUBLICATIONS

Yang et al., "Automatic Liver Segmentation Using an Adversarial Image-to-Image Network," 2017, Medical Image Computing and Computer Assisted Intervention—MICCAI 2017, Lecture Notes in Computer Science, vol. 10435, pp. 507-515.

O'Reilly, "Philips introduces next generation of Advanced Visualization Workspace—IntelliSpace Portal 12—with AI capabilities at RSNA 2020," 2020, retrieved online at https://www.philips.com/a-w/about/news/archive/standard/news/press/2020/20201130-philips-introduces-next-generation-of-advanced-visualization-workspace-intellispace-portal-12-with-ai-capabilities-at-rsna-2020.html, 11 pgs.

Cerny et al., "LI-RADS Version 2018 Ancillary Features at MRI," 2018, RadioGraphics, vol. 38. pp. 1973-2001.

Letter from Food and Drug Administration to Siemens Medical Solutions, Inc. dated Nov. 13, 2014, re: syngo.CT Liver Analysis, retrieved at https://www.accessdata.fda.gov/cdrh_docs/pdf13/K133643.pdf, 12 pgs.

Letter from Food and Drug Administration to GE Medical Systems SCS dated Mar. 20, 2020, re: Hepatic VCAR, retrieved at https://www.accessdata.fda.gov/cdrh_docs/pdf19/K193281.pdf, 6 pgs.

* cited by examiner

Receive a plurality of medical images of one or more lesions
202

Identify a modality, a sequence, a phase, and a time point associated with each of the plurality of medical images
204

Segment anatomical objects of interest from each of the plurality of medical images based on the modalities, the sequences, and the phases
206

Segment the one or more lesions from each of the plurality of medical images based on the modalities, the sequences, and the phases to generate a set of candidate masks
208

Register certain medical images from the plurality of medical images to generate registration transformations
210

Perform one or more assessments of the one or more lesions based on the segmented anatomical objects of interest, the segmented one or more lesions, and the registration transformations
212

Output the set of candidate masks, the registration transformations, and results of the one or more assessments of the one or more lesions
214

| Time | Modality | Diameter (mm x mm) / volume (mm³) | Location (Segment) | Series / Slice Range | Threshold growth (to prior exam) | LI-RADS features | LI-RADS category |
|---|---|---|---|---|---|---|---|
| 2020-01-20 | MR | 7 x 7 / 420 | II + III | x.xx.xxx / 30-37 | N/A | APHE: Yes<br>Washout: No<br>Capsule: No | LR - 4 |
| 2020-05-20 | CT | 6 x 6 / 350 | II | y.yy.yyy / 53-59 | Progress | APHE: Yes<br>Washout: No<br>Capsule: No | LR - 4 |
| 2020-09-20 | CT | 5 x 5 / 230 | II | z.zz.zzz / 52-57 | Progress | APHE: Yes<br>Washout: No<br>Capsule: No | LR - 3 |

| Whole Liver | 2000 | Segment I | 30 | Segment V | 330 |
|---|---|---|---|---|---|
| Hepatic artery | 20 | Segment II | 140 | Segment VI | 180 |
| Hepatic vein | 50 | Segment III | 150 | Segment VII | 380 |
| Portal vein | 40 | Segment IVa | 170 | Segment VIII | 440 |
|  |  | Segment IVb | 180 |  |  |

AI DRIVEN LONGITUDINAL LIVER FOCAL LESION ANALYSIS

TECHNICAL FIELD

The present invention relates generally to liver focal lesion analysis, and in particular to AI (artificial intelligence) driven longitudinal liver focal lesion analysis.

BACKGROUND

Focal liver lesions are abnormal solid or cystic masses of the liver. Analysis of focal liver lesions is an important but complex clinical procedure. Conventionally, liver focal lesion analysis is performed by a radiologist manually evaluating a series of imaging studies of a lesion of a patient acquired over multiple time points. Each imaging study may comprise a plurality of medical images acquired for different sequences and contrast phases to capture characteristics of the lesion from various perspectives. The radiologist evaluates the imaging studies by annotating each focal lesion, reporting the location of the focal lesions, monitoring the volume and diameter of the focal lesions longitudinally over the multiple time points, and characterizing the type of the focal lesions based on visual patterns over medical images of different sequences or contrast phases. Such manual analysis of liver focal lesions is a time-consuming and labor-intensive process and may reflect variances due to errors or the subjective interpretation by the radiologist. Recently, AI (artificial intelligence) has been applied to liver segmentation for liver focal lesion analysis. However, such AI based approaches require a relatively high amount of user input and are computationally intensive.

BRIEF SUMMARY OF THE INVENTION

In accordance with one or more embodiments, systems and methods for lesion analysis are provided that reduce the amount of user input required and are not computationally intensive, as compared to conventional approaches.

In accordance with one or more embodiments, a plurality of input medical images of a lesion is received. The plurality of input medical images comprises an initial input medical image and one or more additional input medical images. The initial input medical image comprises a region of interest around the lesion. A mask of the lesion is curated for the initial input medical image based on the region of interest and a set of candidate masks. The region of interest in the initial input medical image is propagated to the one or more additional input medical images based on prior registration transformations. A mask of the lesion is curated for each of the one or more additional input medical images based on the propagated regions of interest and the set of candidate masks. One or more assessments of the lesion are performed based on the mask for the initial input medical image, the masks for the one or more additional input medical images, and prior assessments of lesions. Results of the one or more assessments of the lesion are output.

In one embodiment, the mask of the lesion for the initial input medical image is curated by comparing the lesion with each candidate mask in the set of candidate masks and selecting a candidate mask from the set of candidate masks as the mask of the lesion based on the comparing. User input adjusting the selected candidate mask may be received.

In one embodiment, the one or more assessments of the lesion are performed by modifying one or more of the prior assessments of the lesions. In one embodiment, the one or more assessments of the lesion are performed by determining a volume and a diameter of the lesion or by characterizing the lesion across sequences, phases, and time points of the plurality of input medical images.

In one embodiment, a plurality of medical images of one or more lesions is received. A modality, a sequence, a phase, and a time point associated with each of the plurality of medical images are received. Anatomical objects of interest are segmented from each of the plurality of medical images based on the modalities, the sequences, the phases, and the time points. The one or more lesions are segmented from each of the plurality of medical images based on the modalities, the sequences, the phases, and the time points to generate the set of candidate masks. Certain medical images from the plurality of images are registered to generate the prior registration transformations. One or more assessments of the one or more lesions are performed based on the segmented anatomical objects of interest, the segmented one or more lesions, and the prior registration transformations to generate the prior assessments of lesions.

In one embodiment, the initial input medical image is an image of the plurality of input medical images acquired at a first time point and the one or more additional medical images are images of the plurality of input medical images acquired at subsequent time points. The plurality of input medical images may comprise images acquired for different sequences and contrast phases.

These and other advantages of the invention will be apparent to those of ordinary skill in the art by reference to the following detailed description and the accompanying drawings.

BRIEF DESCRIPTION OF THE DRAWINGS

FIG. 2 shows a method for preprocessing medical images during an offline stage for longitudinal lesion analysis, in accordance with one or more embodiments;

FIG. 4 shows an exemplary structured report of a lesion selected by user input, in accordance with one or more embodiments;

FIG. 5 shows an exemplary structured report of computed volumetry (in cubic millimeters), in accordance with one or more embodiments;

DETAILED DESCRIPTION

The present invention generally relates to methods and systems for AI (artificial intelligence) driven longitudinal liver focal lesion analysis. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
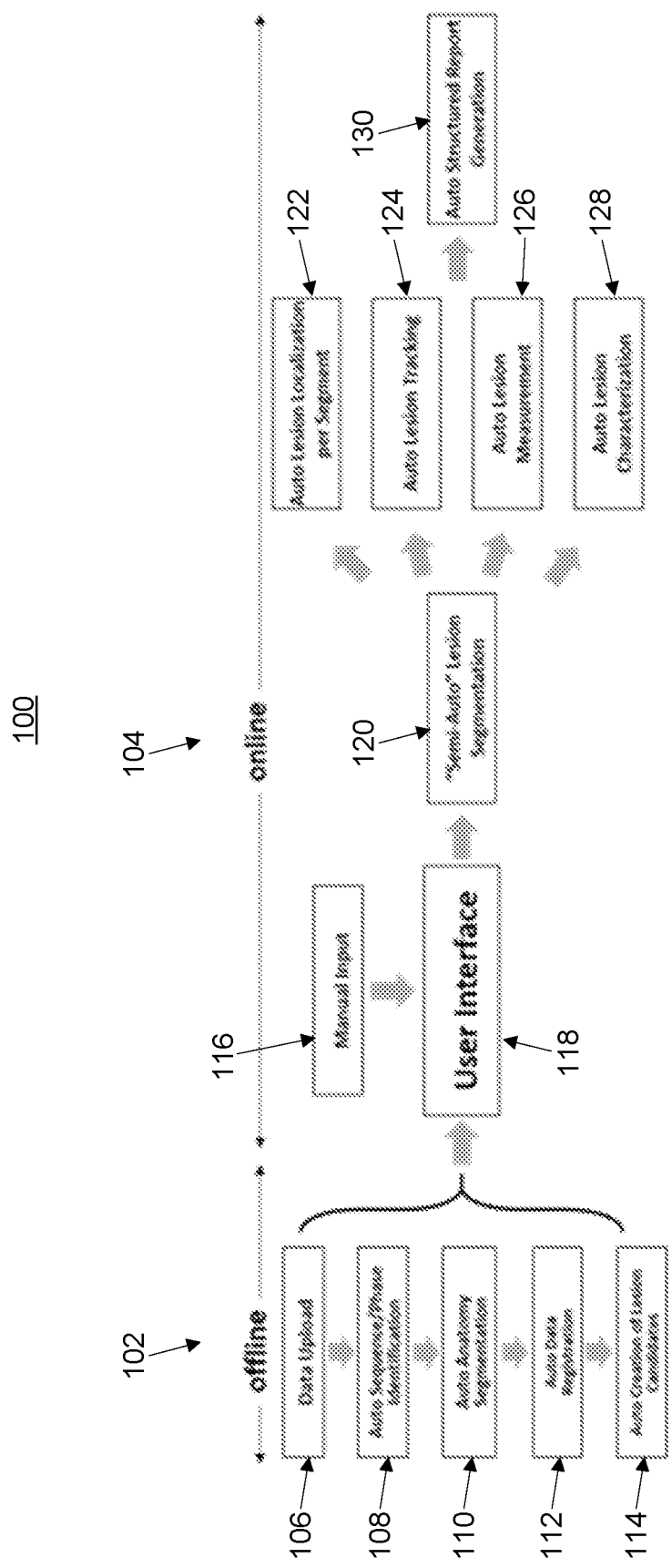
FIG. 1 shows a workflow for longitudinal lesion analysis, in accordance with one or more embodiments.

FIG. 1 shows a workflow 100 for longitudinal lesion analysis, in accordance with one or more embodiments. Longitudinal lesion analysis in workflow 100 comprises two stages: an offline stage 102 and an online stage 104. In offline stage 102, steps 106-114 are performed to preprocess a plurality of medical images using a variety of machine learning based networks to generate various preprocessing data. Such preprocessing data may comprise, for example, candidate lesion masks, liver and liver segment segmentation masks, registration transformations between medical images across different time points and across different sequences and/or contrast phases within a time point, and measures of interest (e.g., volumes of the liver, of the left/right liver lobes, of the functional segments of the vessels, and of the vessels). Once offline stage 102 is complete, online stage 104 may be repeatedly performed any number of times for longitudinal liver focal lesion analysis of different input medical images. In online stage 104, steps 116-130 are performed for longitudinal lesion analysis of input medical images using the preprocessing data. The longitudinal lesion analysis is performed by leveraging or analyzing the preprocessing data instead of having to apply machine learning based networks for performing an assessment of the lesions. While offline stage 102 employs various machine learning based networks that are relatively computationally intensive, online stage 104 does not employ as many machine learning based networks and is therefore less computationally intensive. Offline stage 102 will be further described below in connection with FIG. 2. Online stage 104 will be further described below in connection with FIG. 3.

Advantageously, embodiments described herein provide for longitudinal liver focal lesion analysis with less computational complexity and minimal user interaction. Further, embodiments described herein generate longitudinal liver focal lesions analysis reports to improve radiologists' efficiency, and provide for consistent and reproducible measurements. Embodiments described herein may be efficiently integrated into existing clinical workflows due to its linear design.

FIG. 2 shows a method 200 for preprocessing medical images during an offline stage for longitudinal lesion analysis, in accordance with one or more embodiments. The steps of method 200 may be performed by one or more suitable computing devices, such as, e.g., computer 802 of FIG. 8. The steps of method 200 are performed during a prior offline stage. FIG. 2 will be described with reference to offline stage 102 of FIG. 1.

At step 202 of FIG. 2, a plurality of medical images of one or more lesions is received. In one example, as shown in FIG. 1, the plurality of medical images is received at data upload step 106 of offline stage 102. The plurality of medical images may comprise medical images acquired for different sequences and/or contrast phases, which may correspond to different imaging studies acquired at a plurality of time points, to capture characteristics of the one or more lesions from various perspectives. The sequences may be of an MRI (magnetic resonance imaging) acquisition acquired using different configurations of radiofrequency pulses and gradients (e.g., T1-weighted, T2-weighted, diffusion weighted, etc.). Different types of lesions may appear in different intensity attenuation with respect to healthy tissue in each MRI sequence. The contrast phases relate to the contrast agent utilized during image acquisition. For CT (computed tomography) and MRI T1-weighted studies, multiple acquisitions of images are performed before and after the injection of the contrast agent, typically including pre-contrast, arterial, portal venous, and delayed phases. Different types of lesions appear in different intensity attenuation with respect to health tissue across contrast phases. Different types of lesions also have different wash out behavior in intensity attenuation across contrast phases. The one or more lesions may be focal lesions of a liver of a patient.

In one embodiment, the plurality of medical images comprises MRI and/or CT images. However, the plurality of medical images may comprise images of any other suitable modality, such as, e.g., ultrasound, x-ray, or any other medical imaging modality or combinations of medical imaging modalities. The plurality of medical images may comprise 2D (two dimensional) images and/or 3D (three dimensional) volumes. The plurality of medical images may be received directly from an image acquisition device, such as, e.g., a CT scanner, as the medical images are acquired, or can be received by loading previously acquired medical images from a storage or memory of a computer system (e.g., a PACS (picture archiving and communication system)) or receiving medical images that have been transmitted from a remote computer system.

At step 204 of FIG. 2, a modality, a sequence, a phase, and a time point associated with each of the plurality of medical images are identified. In one example, as shown in FIG. 1, the modality, the sequence, the phase, and the time point associated with each of the plurality of medical images is identified at auto sequence/phase identification step 108 of offline stage 102. In one embodiment, the sequence, phase, and time point can be identified by retrieving the meta-information from the original medical images (e.g., DICOM (digital imaging and communications in medicine) series information). A pre-built dictionary can be used for each sequence and phase to be identified, and the dictionary can be adapted and/or extended based on the DICOM series information conventions on the sites to be deployed. The time point retrieval can be specifically based on the DICOM tag of acquisition time as complimentary information to the dictionary-based contrast phase identification. In another embodiment, the sequence and contrast phase identification can be performed using a classification neural network given properly trained models. The modality, the sequence, the phase, and the time point associated with each of the plurality of medical images may be identified using any other suitable approach.

At step 206 of FIG. 2, anatomical objects of interest are segmented from each of the plurality of medical images based on the modalities, the sequences, and the phases, and, at step 208 of FIG. 2, the one or more lesions are segmented from each of the plurality of medical images based on the modalities, the sequences, and the phases to generate a set of candidate masks. In one example, as shown in FIG. 1, the anatomical objects of interest and the one or more lesions are segmented at auto anatomy segmentation step 110 of offline stage 102. The anatomical objects of interest may be, for example, the liver, liver segments, vessels, or any other suitable anatomical object of interest.

The segmentations may be performed using any suitable approach. In one embodiment, the segmentations are performed using one or more machine learning based segmentation networks trained for a particular modality, sequence, and/or phase. The anatomical objects of interest and the one or more lesions may be segmented from the plurality of medical images at each of the time points. The segmented anatomical objects of interest and the segmented one or more lesions may be in any suitable format. For example, the segmented anatomical objects of interest and the segmented one or more lesions may be probability maps (or heat maps) where each respective pixel is assigned a value indicating a probability that the respective pixel depicts the anatomical object of interest or the one or more lesions. In another example, the segmented anatomical objects of interest and the segmented one or more lesions may be binary segmentation masks where each respective pixel is assigned a value indicating a whether or not the respective pixel depicts the anatomical object of interest or the one or more lesions.

At step 210 of FIG. 2, certain medical images from the plurality of medical images are registered to generate registration transformations. In one example, as shown in FIG. 1, the registration is performed at auto data registration step 112 of offline stage 102. The registration is performed between certain medical images across the sequences and/or the phases within each of the time points and between certain medical images across the time points. The registration transformations represent relationships between corresponding points in the certain medical images. The registration may be performed using any suitable, known approach. For example, the registration may be performed by a series of iterative processes to align the image content of two images driven by a similarity metric, such as, e.g., normalized cross correlation, or mutual information. The registration process usually starts with a rigid transform for rough alignment and followed up with a deformable transform for refinement. In another example, the registration can be also performed using a machine learning network given a properly trained model.

At step 212 of FIG. 2, one or more assessments of the one or more lesions are performed based on the segmented anatomical objects of interest, the segmented one or more lesions, and the registration transformations. The one or more assessments may be any suitable assessment of the one or more lesions.

In one embodiment, the one or more assessments are performed by computing one or more measures of interest. For example, the one or more measures of interest may be calculated as a volume of the lesion, a volume of the liver and a volume of the functional liver segments. The volume of the lesion, the volume of the liver and the volume of the functional liver segments may be respectively calculated as a volume of the segmented legion, a volume of the segmented liver and a volume of the segmented functional liver segments.

In one embodiment, the one or more assessments are performed by characterizing the segmented one or more lesions by its features across the sequences and/or the phases and across the time points. For example, the characterization of the segmented one or more lesions may comprise the lesion size, the lesion size change across the time points, the presence of the liver capsule or rim, hyper- or hypo-intensity, enhancement characteristics, and ancillary features.

At step 214 of FIG. 2, the set of candidate masks, the registration transformations, and results of the one or more assessments of the one or more lesions are output. Any other suitable data generated during method 200 may also be output. For example, in one embodiment, an organized data structure of the plurality of medical images organized based on the modality, the sequence, the phase, and the time points is also output. In another embodiment, the segmented anatomical objects of interest (e.g., the segmented liver and liver segments) at each of the time points are also output. Each of the one or more lesions may have a unique index indicating a lesion ID. In one example, as shown in FIG. 1, the output of data is performed at auto creation of lesion candidates step 114 of offline stage 102.

Figure 3:
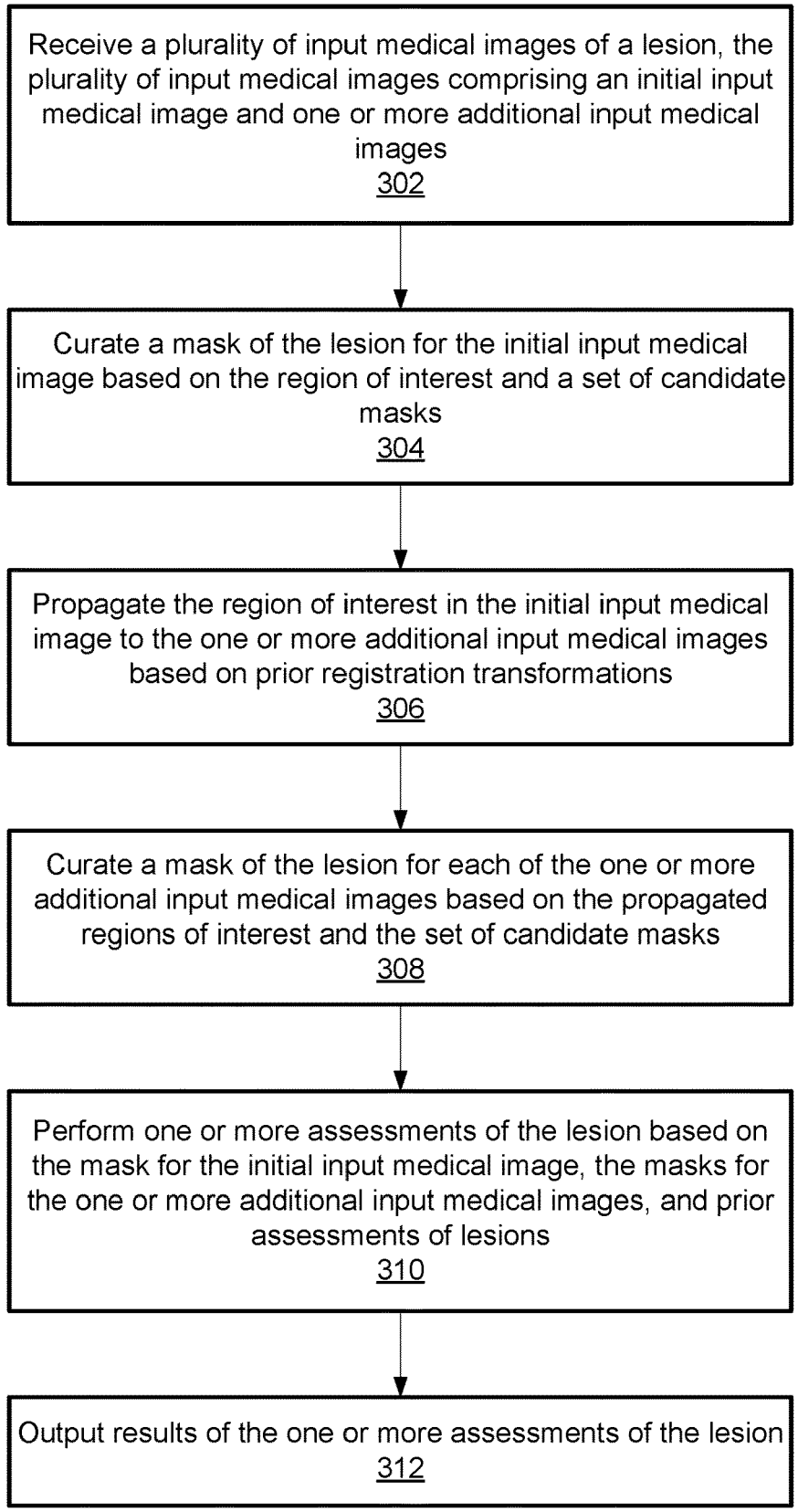
FIG. 3 shows a method for longitudinal lesion analysis during an online stage, in accordance with one or more embodiments.

FIG. 3 shows a method 300 for longitudinal lesion analysis during an online stage, in accordance with one or more embodiments. The steps of method 300 may be performed by one or more suitable computing devices, such as, e.g., computer 802 of FIG. 8. The steps of method 300 are performed during an online stage based on preprocessed data (e.g., generated according to method 200 of FIG. 2). The steps of method 300 may be repeatedly performed any number of times for different input medical images. FIG. 3 will be described with reference to online stage 104 of FIG. 1.

At step 302 of FIG. 3, a plurality of input medical images of a lesion is received. The plurality of input medical images received at step 302 are the same images utilized during the offline stage (e.g., received at step 202 of FIG. 2). The plurality of input medical images comprises an initial input medical image and one or more additional input medical images. The initial input medical image may correspond to the input medical image, of the plurality of input medical images, acquired at a first time point and the one or more additional input medical images may correspond to input medical images, of the plurality of input medical images, acquired at subsequent time points. The plurality of input medical images may comprise medical images acquired for different sequences and/or contrast phases. The lesion may be focal lesion of a liver of a patient.

The initial input medical image comprises a region of interest around the lesion. In one embodiment, user input may be received identifying the region of interest. In another embodiment, the region of interest is automatically identified. The region of interest may be, for example, a bounding box. In one example, as shown in FIG. 1, the plurality of input medical images and user input defining the region of interest are received by manual input 116 via user interface 118 of online stage 104.

In one embodiment, the input medical images comprise MRI and/or CT images. However, the input medical images may comprise images of any other suitable modality, such as, e.g., ultrasound, x-ray, or any other medical imaging modality or combinations of medical imaging modalities. The input medical images may comprise 2D images and/or 3D volumes. The input medical images may be received directly from an image acquisition device, such as, e.g., a CT scanner, as the medical images are acquired, or can be received by loading previously acquired medical images from a storage or memory of a computer system (e.g., a PACS) or receiving medical images that have been transmitted from a remote computer system.

At step 304 of FIG. 3, a mask of the lesion for the initial input medical image is curated based on the region of interest and a set of candidate masks. As used herein, the term "curate" refers to the selection or generation of, e.g., the mask of the lesion, from the set of candidate masks. In one example, as shown in FIG. 1, the mask of the lesion for the initial input medical image is curated at "semi-auto" lesion segmentation step 120 of online stage 104. The set of candidate masks are generated or pre-computed during the offline stage (e.g., at step 208 of FIG. 2).

In one embodiment, the mask of the lesion for the initial input medical image is curated by comparing the lesion with each candidate mask in the set of candidate masks. The set of candidate mask includes multiple lesion candidates pre-computed in the offline stage, distributed over the range of the entire liver. During the comparison, the region of interest, defined by a user, narrows the scope to a much smaller area, so that candidate masks of individual candidate lesions that overlap with this ROI would be selected as the mask of the lesion. The selected candidate mask can be adjusted (e.g., in size and/or shape) based on user input from the user (e.g., via a slider). For example, the candidate mask can be in a probabilistic form so that the size of the final lesion mask can be adjusted using, e.g., a threshold on the probabilities.

At step 306 of FIG. 3, the region of interest in the initial input medical image is propagated to the one or more additional input medical images based on prior registration transformation. In one example, as shown in FIG. 1, the region of interest in the initial input medical image is propagated to the one or more additional input medical images at "semi-auto" lesion segmentation step 120 of online state 104. The prior registration transformations are generated during the offline stage (e.g., at step 210 of FIG. 2). The region of interest in the initial input medical image is propagated to the one or more additional input medical images by applying the prior registration transformations to the location of the region of interest in the initial input medical image to identify corresponding locations of the region of interest in the one or more additional input medical images.

At step 308 of FIG. 3, a mask of the lesion for each of the one or more additional input medical images is curated based on the propagated regions of interest and the set of candidate masks. In one example, as shown in FIG. 1, the mask of the lesion for each of the one or more additional input medical images is curated at "semi-auto" lesion segmentation step 120 of online stage 104. The mask of the lesion for each of the one or more additional input medical images may be curated as described in step 304 of FIG. 3.

At step 310 of FIG. 3, one or more assessments of the lesion is performed based on the mask for the initial input medical image, the masks for the one or more additional input medical images, and prior assessments of lesions. The prior assessments are performed during the offline stage (e.g., at step 212 of FIG. 2). The assessment of the lesion may comprise any suitable assessment or assessments of the lesion. In one embodiment, the one or more assessments may be performed by modifying the prior assessments of the lesions. The modification of prior assessments can be, for example, (1) adjusting the threshold of the probability of the candidate mask, (2) using mask editing tools for refinement, (3) rejecting the prior assessment and drawing the mask from scratch, etc.

In one embodiment, the one or more assessments of the lesion may comprise localizing the lesion per segment of the liver. In one example, localizing the lesion is performed at auto lesion localization per segment step 122 of online stage 104. In one embodiment, the one or more assessments of the lesion may comprise tracking the lesion across the plurality of input medical images, e.g., by assigning labels according to the masks of the lesion. The lesion localization may be performed by examining which liver segment (pre-computed during the offline stage) the lesion falls in. One approach can be identifying the segment area with maximum overlap area with the lesion mask. In one example, tracking the lesion is performed at auto lesion tracking step 124 of online stage 104. Lesion tracking is performed for identifying the corresponding lesion across multiple studies. It is done implicitly as the user defined ROI is propagated to each of the follow-up studies (at step 306), where each ROI (including the ROI defined in the initial input medical image and the propagated ROIs in the additional input medical images) generate an individual lesion mask for the associated study. These individual lesion masks belong to the same entity across studies by this design. In one embodiment, the one or more assessments of the lesion may comprise computing one or more measures of interest. For example, the one or more measures of interest may be a volume and a diameter of the lesion at each time point. In one example, computing one or more measures of interest is performed at auto lesion measurement step 126 of online stage 104. In one embodiment, the one or more assessments of the lesion may comprise characterizing the lesion by its features across the sequences and/or the phases and across the time points. For example, the characterization of the lesion may comprise the lesion size, the lesion size change across the time points, the presence of the liver capsule or rim, hyper- or hypo-intensity, enhancement characteristics, and ancillary features. In one example, characterizing the lesion is performed at auto lesion characterization step 128 of online stage 104. The one or more assessments may comprise any other suitable assessment of the one or more lesions.

In one embodiment, the one or more assessments of the lesion comprises a structured report. The structured report is generated comprising the one or more other assessments of the lesion. In one example, the structured report is generated at auto structured report generation step 130 of online stage 104. FIG. 4 shows an exemplary structured report 400 of a lesion selected by user input, in accordance with one or more embodiments. Structured report 400 is a table identifying times input medical images were acquired, modalities of the input medical images, a diameter of the lesion in the input medical images, a series/slice range of the input medical images, a threshold growth (to prior exam) of the lesion in the input medical images, LI-RADS (liver reporting and data system) features for the lesion in the input medical images, and LI-RADS category for the lesion in the input medical images. FIG. 5 shows an exemplary structured report 500 of computed volumetry (in cubic millimeters), in accordance with one or more embodiments. Structured report 500 comprises a table identifying volumes for the whole liver, the hepatic artery, the hepatic vein, the portal vein, and segments I-VIII of the liver.

At step 312 of FIG. 3, results of the one or more assessments of the lesion are output. For example, the one or more assessments of the lesion can be output by displaying the one or more assessments of the lesion on a display device of a computer system, storing the one or more assessments of the lesion on a memory or storage of a computer system, or by transmitting the one or more assessments of the lesion to a remote computer system.

In one embodiment, the one or more assessments of the lesion are output on a user interface, such as, e.g., user interface 118 of FIG. 1. The user interface may enable the following features: 1) data uploading and management, 2) MPR (multiplanar reformation) and segmentation surface rendering, 3) quick access to any sequence or phase within a single imaging study, 4) quick access to another imaging study at a different time point, 5) simultaneous display of multiples image series from two or more sequences or phases or two or more imaging studies at different time points with synchronized location, 6) visibility toggle for each segmentation of the anatomical object of interest or lesion, 7) manual input to define the region of interest for lesion selection (e.g., via mouse click), 8) adaptation of the lesion segmentation based on a threshold on the segmentation probability map, where the threshold value can be manually adjusted (e.g., by a slider), 9) editable lesion location based on the liver segment, 10) editable lesion characterization, 11) editable lesion contour, 12) lesion statistics display (e.g., volume size, diameter, etc.) to show a singe time point or to show a summary of multiple time points, 13) a list of processed lesions which can be selected to center images to the selected lesion with statistics displayed, and 14) statistics confirmation and report export.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 6:
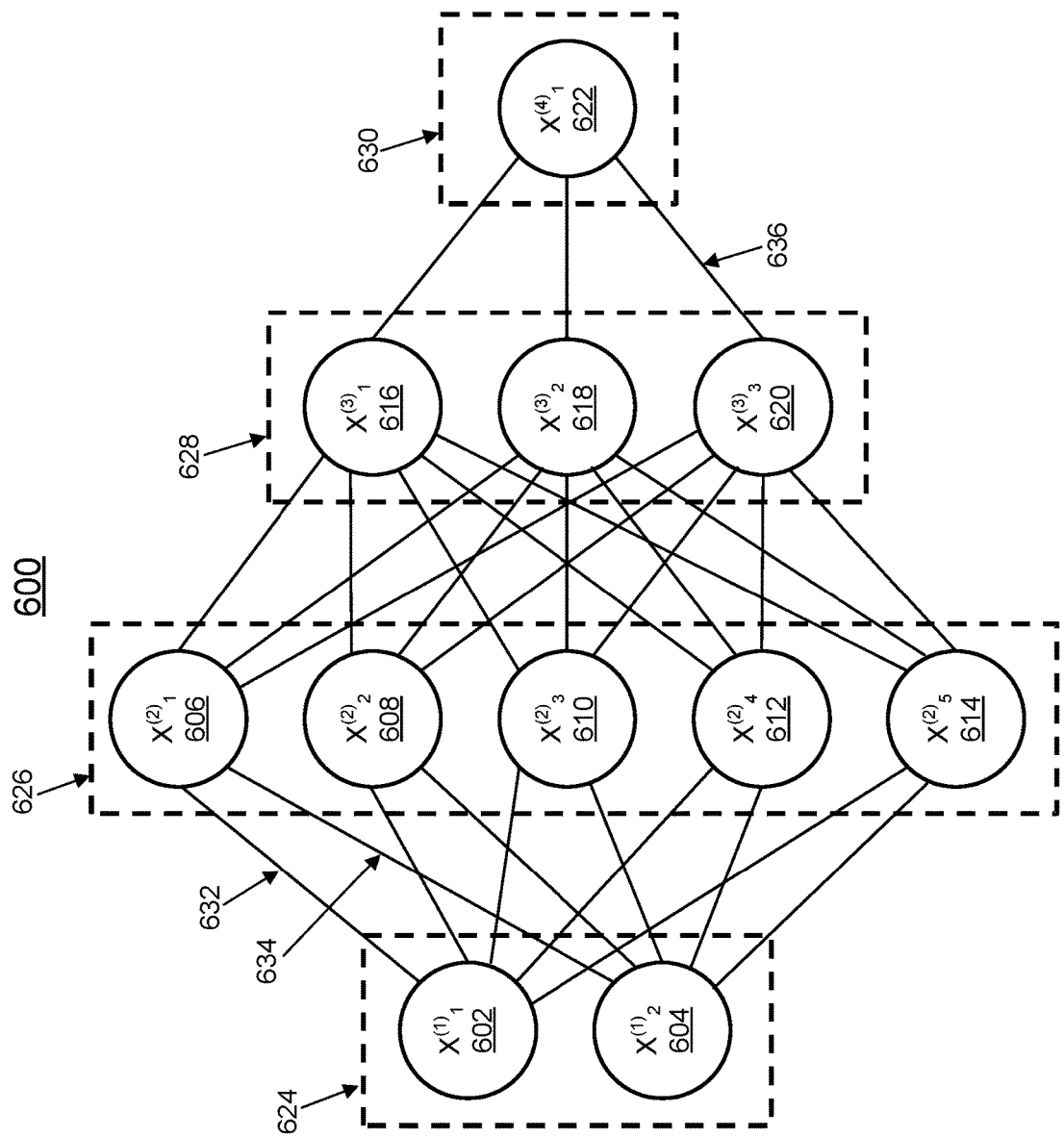
FIG. 6 shows an exemplary artificial neural network that may be used to implement one or more embodiments.

FIG. 6 shows an embodiment of an artificial neural network 600, in accordance with one or more embodiments. Alternative terms for "artificial neural network" are "neural network", "artificial neural net" or "neural net". Machine learning networks described herein may be implemented using artificial neural network 600.

The artificial neural network 600 comprises nodes 602-622 and edges 632, 634, . . . , 636, wherein each edge 632, 634, . . . , 636 is a directed connection from a first node 602-622 to a second node 602-622. In general, the first node 602-622 and the second node 602-622 are different nodes 602-622, it is also possible that the first node 602-622 and the second node 602-622 are identical. For example, in FIG. 6, the edge 632 is a directed connection from the node 602 to the node 606, and the edge 634 is a directed connection from the node 604 to the node 606. An edge 632, 634, . . . , 636 from a first node 602-622 to a second node 602-622 is also denoted as "ingoing edge" for the second node 602-622 and as "outgoing edge" for the first node 602-622.

In this embodiment, the nodes 602-622 of the artificial neural network 600 can be arranged in layers 624-630, wherein the layers can comprise an intrinsic order introduced by the edges 632, 634, . . . , 636 between the nodes 602-622. In particular, edges 632, 634, . . . , 636 can exist only between neighboring layers of nodes. In the embodiment shown in FIG. 6, there is an input layer 624 comprising only nodes 602 and 604 without an incoming edge, an output layer 630 comprising only node 622 without outgoing edges, and hidden layers 626, 628 in-between the input layer 624 and the output layer 630. In general, the number of hidden layers 626, 628 can be chosen arbitrarily. The number of nodes 602 and 604 within the input layer 624 usually relates to the number of input values of the neural network 600, and the number of nodes 622 within the output layer 630 usually relates to the number of output values of the neural network 600.

In particular, a (real) number can be assigned as a value to every node 602-622 of the neural network 600. Here, $x^{(n)}_i$ denotes the value of the i-th node 602-622 of the n-th layer 624-630. The values of the nodes 602-622 of the input layer 624 are equivalent to the input values of the neural network 600, the value of the node 622 of the output layer 630 is equivalent to the output value of the neural network 600. Furthermore, each edge 632, 634, . . . , 636 can comprise a weight being a real number, in particular, the weight is a real number within the interval [−1, 1] or within the interval [0, 1]. Here, $w^{(m,n)}_{i,j}$ denotes the weight of the edge between the i-th node 602-622 of the m-th layer 624-630 and the j-th node 602-622 of the n-th layer 624-630. Furthermore, the abbreviation $w^{(n)}_{i,j}$ is defined for the weight $w^{(n,n+1)}_{i,j}$.

In particular, to calculate the output values of the neural network 600, the input values are propagated through the neural network. In particular, the values of the nodes 602-622 of the (n+1)-th layer 624-630 can be calculated based on the values of the nodes 602-622 of the n-th layer 624-630 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 624 are given by the input of the neural network 600, wherein values of the first hidden layer 626 can be calculated based on the values of the input layer 624 of the neural network, wherein values of the second hidden layer 628 can be calculated based in the values of the first hidden layer 626, etc.

In order to set the values $w^{(m,n)}_{i,j}$ for the edges, the neural network 600 has to be trained using training data. In particular, training data comprises training input data and training output data (denoted as $t_i$). For a training step, the neural network 600 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 600 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein $\gamma$ is a learning rate, and the numbers $\delta^{(n)}_j$ can be recursively calculated as $$\delta^{(n)}_j = (\Sigma_k \delta^{(n+1)}_k \cdot w^{(n+1)}_{j,k}) \cdot f'(\Sigma_i x^{(n)}_i \cdot w^{(n)}_{i,j})$$

based on $\delta^{(n+1)}_j$, if the (n+1)-th layer is not the output layer, and $$\delta^{(n)}_j = (x^{(n+1)}_k - t^{(n+1)}_j) \cdot f'(\Sigma_i x^{(n)}_i \cdot w^{(n)}_{i,j})$$

if the (n+1)-th layer is the output layer 630, wherein f' is the first derivative of the activation function, and $y^{(n+1)}_j$ is the comparison training value for the j-th node of the output layer 630.

Figure 7:
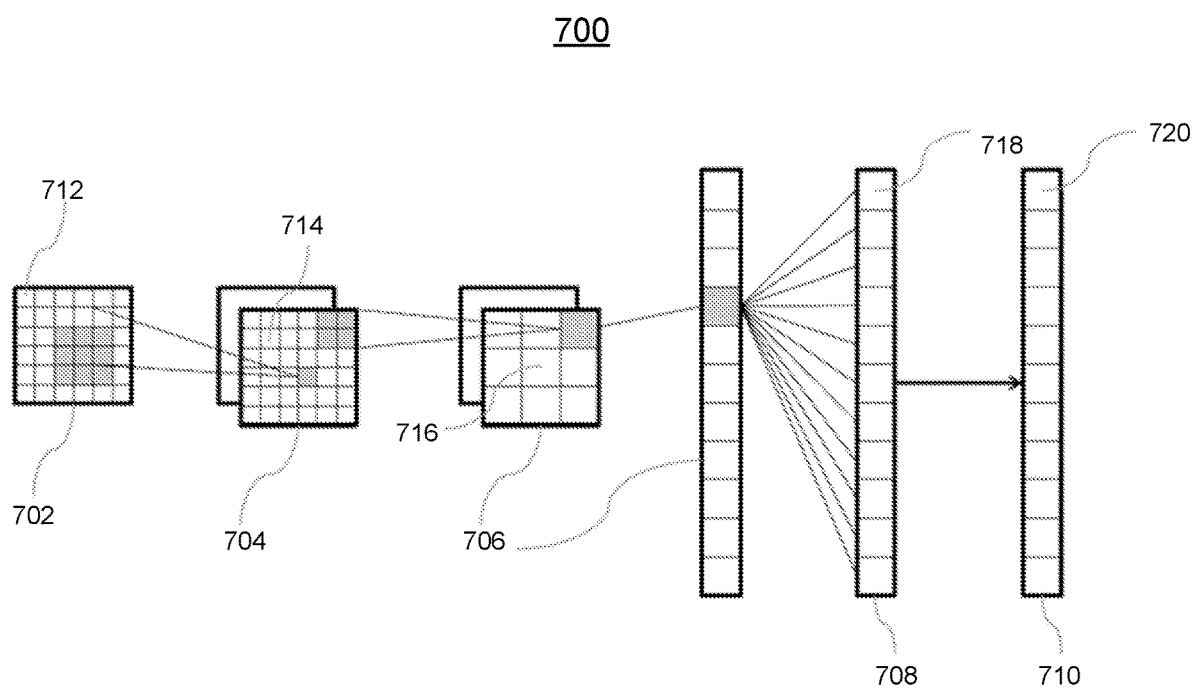
FIG. 7 shows a convolutional neural network that may be used to implement one or more embodiments.

FIG. 7 shows a convolutional neural network 700, in accordance with one or more embodiments. Machine learning networks described herein may be implemented using convolutional neural network 700.

In the embodiment shown in FIG. 7, the convolutional neural network comprises 700 an input layer 702, a convolutional layer 704, a pooling layer 706, a fully connected layer 708, and an output layer 710. Alternatively, the convolutional neural network 700 can comprise several convolutional layers 704, several pooling layers 706, and several fully connected layers 708, as well as other types of layers. The order of the layers can be chosen arbitrarily, usually fully connected layers 708 are used as the last layers before the output layer 710.

In particular, within a convolutional neural network 700, the nodes 712-720 of one layer 702-710 can be considered to be arranged as a d-dimensional matrix or as a d-dimensional image. In particular, in the two-dimensional case the value of the node 712-720 indexed with i and j in the n-th layer 702-710 can be denoted as $x^{(n)}_{[i,j]}$. However, the arrangement of the nodes 712-720 of one layer 702-710 does not have an effect on the calculations executed within the convolutional neural network 700 as such, since these are given solely by the structure and the weights of the edges.

In particular, a convolutional layer 704 is characterized by the structure and the weights of the incoming edges forming a convolution operation based on a certain number of kernels. In particular, the structure and the weights of the incoming edges are chosen such that the values $x^{(n)}_k$ of the nodes 714 of the convolutional layer 704 are calculated as a convolution $x^{(n)}_k = K_k * x^{(n-1)}$ based on the values $x^{(n-1)}$ of the nodes 712 of the preceding layer 702, where the convolution * is defined in the two-dimensional case as $$x^{(n)}_k[i,j] = (K_k * x^{(n-1)})[i,j] = \Sigma_i \Sigma_j K_k[i',j'] \cdot x^{(n-1)}[i-i',j-j']$$

Here the k-th kernel $K_k$ is a d-dimensional matrix (in this embodiment a two-dimensional matrix), which is usually small compared to the number of nodes 712-718 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 712-720 in the respective layer 702-710. In particular, for a convolutional layer 704, the number of nodes 714 in the convolutional layer is equivalent to the number of nodes 712 in the preceding layer 702 multiplied with the number of kernels.

If the nodes 712 of the preceding layer 702 are arranged as a d-dimensional matrix, using a plurality of kernels can be interpreted as adding a further dimension (denoted as "depth" dimension), so that the nodes 714 of the convolutional layer 704 are arranged as a (d+1)-dimensional matrix. If the nodes 712 of the preceding layer 702 are already arranged as a (d+1)-dimensional matrix comprising a depth dimension, using a plurality of kernels can be interpreted as expanding along the depth dimension, so that the nodes 714 of the convolutional layer 704 are arranged also as a (d+1)-dimensional matrix, wherein the size of the (d+1)-dimensional matrix with respect to the depth dimension is by a factor of the number of kernels larger than in the preceding layer 702.

The advantage of using convolutional layers 704 is that spatially local correlation of the input data can exploited by enforcing a local connectivity pattern between nodes of adjacent layers, in particular by each node being connected to only a small region of the nodes of the preceding layer.

In embodiment shown in FIG. 7, the input layer 702 comprises 36 nodes 712, arranged as a two-dimensional 6×6 matrix. The convolutional layer 704 comprises 72 nodes 714, arranged as two two-dimensional 6×6 matrices, each of the two matrices being the result of a convolution of the values of the input layer with a kernel. Equivalently, the nodes 714 of the convolutional layer 704 can be interpreted as arranges as a three-dimensional 6×6×2 matrix, wherein the last dimension is the depth dimension.

A pooling layer 706 can be characterized by the structure and the weights of the incoming edges and the activation function of its nodes 716 forming a pooling operation based on a non-linear pooling function f. For example, in the two dimensional case the values $x^{(n)}$ of the nodes 716 of the pooling layer 706 can be calculated based on the values $x^{(n-1)}$ of the nodes 714 of the preceding layer 704 as $$x^{(n)}[i,j] = f(x^{(n-1)}[id_1, jd_2], \ldots, x^{(n-1)}[id_1+d_1-1, jd_2+d_2-1])$$

In other words, by using a pooling layer 706, the number of nodes 714, 716 can be reduced, by replacing a number d1·d2 of neighboring nodes 714 in the preceding layer 704 with a single node 716 being calculated as a function of the values of said number of neighboring nodes in the pooling layer. In particular, the pooling function f can be the max-function, the average or the L2-Norm. In particular, for a pooling layer 706 the weights of the incoming edges are fixed and are not modified by training.

The advantage of using a pooling layer 706 is that the number of nodes 714, 716 and the number of parameters is reduced. This leads to the amount of computation in the network being reduced and to a control of overfitting.

In the embodiment shown in FIG. 7, the pooling layer 706 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 708 can be characterized by the fact that a majority, in particular, all edges between nodes 716 of the previous layer 706 and the nodes 718 of the fully-connected layer 708 are present, and wherein the weight of each of the edges can be adjusted individually.

In this embodiment, the nodes 716 of the preceding layer 706 of the fully-connected layer 708 are displayed both as two-dimensional matrices, and additionally as non-related nodes (indicated as a line of nodes, wherein the number of nodes was reduced for a better presentability). In this embodiment, the number of nodes 718 in the fully connected layer 708 is equal to the number of nodes 716 in the preceding layer 706. Alternatively, the number of nodes 716, 718 can differ.

Furthermore, in this embodiment, the values of the nodes 720 of the output layer 710 are determined by applying the Softmax function onto the values of the nodes 718 of the preceding layer 708. By applying the Softmax function, the sum the values of all nodes 720 of the output layer 710 is 1, and all values of all nodes 720 of the output layer are real numbers between 0 and 1.

A convolutional neural network 700 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 700 can be trained based on the backpropagation algorithm. For preventing overfitting, methods of regularization can be used, e.g. dropout of nodes 712-720, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-3. Certain steps or functions of the methods and workflows described herein, including one or more of the steps or functions of FIGS. 1-3, may be performed by a server or by another processor in a network-based cloud-computing system. Certain steps or functions of the methods and workflows described herein, including one or more of the steps of FIGS. 1-3, may be performed by a client computer in a network-based cloud computing system. The steps or functions of the methods and workflows described herein, including one or more of the steps of FIGS. 1-3, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-3, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 8:
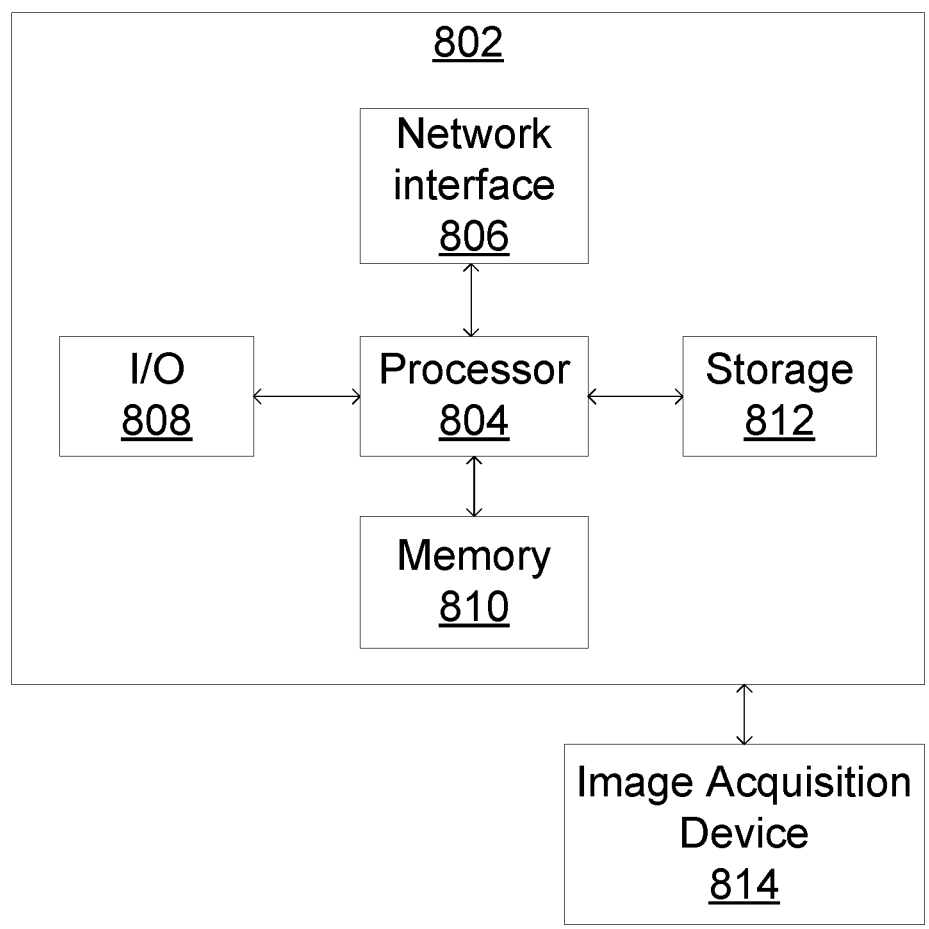
FIG. 8 shows a high-level block diagram of a computer that may be used to implement one or more embodiments.

A high-level block diagram of an example computer 802 that may be used to implement systems, apparatus, and methods described herein is depicted in FIG. 8. Computer 802 includes a processor 804 operatively coupled to a data storage device 812 and a memory 810. Processor 804 controls the overall operation of computer 802 by executing computer program instructions that define such operations. The computer program instructions may be stored in data storage device 812, or other computer readable medium, and loaded into memory 810 when execution of the computer program instructions is desired. Thus, the method and workflow steps or functions of FIGS. 1-3 can be defined by the computer program instructions stored in memory 810 and/or data storage device 812 and controlled by processor 804 executing the computer program instructions. For example, the computer program instructions can be implemented as computer executable code programmed by one skilled in the art to perform the method and workflow steps or functions of FIGS. 1-3. Accordingly, by executing the computer program instructions, the processor 804 executes the method and workflow steps or functions of FIGS. 1-3. Computer 802 may also include one or more network interfaces 806 for communicating with other devices via a network. Computer 802 may also include one or more input/output devices 808 that enable user interaction with computer 802 (e.g., display, keyboard, mouse, speakers, buttons, etc.).

Processor 804 may include both general and special purpose microprocessors, and may be the sole processor or one of multiple processors of computer 802. Processor 804 may include one or more central processing units (CPUs), for example. Processor 804, data storage device 812, and/or memory 810 may include, be supplemented by, or incorporated in, one or more application-specific integrated circuits (ASICs) and/or one or more field programmable gate arrays (FPGAs).

Data storage device 812 and memory 810 each include a tangible non-transitory computer readable storage medium. Data storage device 812, and memory 810, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 808 may include peripherals, such as a printer, scanner, display screen, etc. For example, input/output devices 808 may include a display device such as a cathode ray tube (CRT) or liquid crystal display (LCD) monitor for displaying information to the user, a keyboard, and a pointing device such as a mouse or a trackball by which the user can provide input to computer 802.

An image acquisition device 814 can be connected to the computer 802 to input image data (e.g., medical images) to the computer 802. It is possible to implement the image acquisition device 814 and the computer 802 as one device. It is also possible that the image acquisition device 814 and the computer 802 communicate wirelessly through a network. In a possible embodiment, the computer 802 can be located remotely with respect to the image acquisition device 814.

Any or all of the systems and apparatus discussed herein may be implemented using one or more computers such as computer 802.

One skilled in the art will recognize that an implementation of an actual computer or computer system may have other structures and may contain other components as well, and that FIG. 8 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:
receiving a plurality of input medical images of a lesion, the plurality of input medical images comprising an initial input medical image and one or more additional input medical images, the initial input medical image comprising a region of interest around the lesion;
curating a mask of the lesion for the initial input medical image based on the region of interest and a set of candidate masks;
propagating the region of interest in the initial input medical image to the one or more additional input medical images based on prior registration transformations;
curating a mask of the lesion for each of the one or more additional input medical images based on the propagated regions of interest and the set of candidate masks;
performing one or more assessments of the lesion based on the mask for the initial input medical image, the masks for the one or more additional input medical images, and prior assessments of lesions; and
outputting results of the one or more assessments of the lesion.

2. The computer-implemented method of claim 1, wherein curating a mask of the lesion for the initial input medical image based on the region of interest and a set of candidate masks comprises:
comparing the lesion with each candidate mask in the set of candidate masks; and
selecting a candidate mask from the set of candidate masks as the mask of the lesion based on the comparing.

3. The computer-implemented method of claim 2, wherein curating a mask of the lesion for the initial input medical image based on the region of interest and a set of candidate masks further comprises:
receiving user input adjusting the selected candidate mask.

4. The computer-implemented method of claim 1, wherein performing one or more assessments of the lesion based on the mask for the initial input medical image, the masks for the one or more additional input medical images, and prior assessments of lesions comprises:
modifying one or more of the prior assessments of the lesions.

5. The computer-implemented method of claim 1, wherein performing one or more assessments of the lesion based on the mask for the initial input medical image, the masks for the one or more additional input medical images, and prior assessments of lesions comprises:
determining a volume and a diameter of the lesion.

6. The computer-implemented method of claim 1, wherein performing one or more assessments of the lesion based on the mask for the initial input medical image, the masks for the one or more additional input medical images, and prior assessments of lesions comprises:
characterizing the lesion across sequences, phases, and time points of the plurality of input medical images.

7. The computer-implemented method of claim 1, further comprising:
receiving a plurality of medical images of one or more lesions;

identifying a modality, a sequence, a phase, and a time point associated with each of the plurality of medical images;

segmenting anatomical objects of interest from each of the plurality of medical images based on the modalities, the sequences, the phases, and the time points;

segmenting the one or more lesions from each of the plurality of medical images based on the modalities, the sequences, the phases, and the time points to generate the set of candidate masks;

registering certain medical images from the plurality of images to generate the prior registration transformations; and performing one or more assessments of the one or more lesions based on the segmented anatomical objects of interest, the segmented one or more lesions, and the prior registration transformations to generate the prior assessments of lesions.

8. The computer-implemented method of claim 1, wherein the initial input medical image is an image of the plurality of input medical images acquired at a first time point and the one or more additional medical images are images of the plurality of input medical images acquired at subsequent time points.

9. The computer-implemented method of claim 1, wherein the plurality of input medical images comprises images acquired for different sequences and contrast phases.

10. An apparatus comprising:
means for receiving a plurality of input medical images of a lesion, the plurality of input medical images comprising an initial input medical image and one or more additional input medical images, the initial input medical image comprising a region of interest around the lesion;
means for curating a mask of the lesion for the initial input medical image based on the region of interest and a set of candidate masks;
means for propagating the region of interest in the initial input medical image to the one or more additional input medical images based on prior registration transformations;
means for curating a mask of the lesion for each of the one or more additional input medical images based on the propagated regions of interest and the set of candidate masks;
means for performing one or more assessments of the lesion based on the mask for the initial input medical image, the masks for the one or more additional input medical images, and prior assessments of lesions; and
means for outputting results of the one or more assessments of the lesion.

11. The apparatus of claim 10, wherein the means for curating a mask of the lesion for the initial input medical image based on the region of interest and a set of candidate masks comprises:
means for comparing the lesion with each candidate mask in the set of candidate masks; and
means for selecting a candidate mask from the set of candidate masks as the mask of the lesion based on the comparing.

12. The apparatus of claim 11, wherein the means for curating a mask of the lesion for the initial input medical image based on the region of interest and a set of candidate masks further comprises:
means for receiving user input adjusting the selected candidate mask.

13. The apparatus of claim 10, wherein the means for performing one or more assessments of the lesion based on the mask for the initial input medical image, the masks for the one or more additional input medical images, and prior assessments of lesions comprises:
means for modifying one or more of the prior assessments of the lesions.

14. The apparatus of claim 10, wherein the means for performing one or more assessments of the lesion based on the mask for the initial input medical image, the masks for the one or more additional input medical images, and prior assessments of lesions comprises:
means for determining a volume and a diameter of the lesion.

15. A non-transitory computer readable medium storing computer program instructions, the computer program instructions when executed by a processor cause the processor to perform operations comprising:
receiving a plurality of input medical images of a lesion, the plurality of input medical images comprising an initial input medical image and one or more additional input medical images, the initial input medical image comprising a region of interest around the lesion;
curating a mask of the lesion for the initial input medical image based on the region of interest and a set of candidate masks;
propagating the region of interest in the initial input medical image to the one or more additional input medical images based on prior registration transformations;
curating a mask of the lesion for each of the one or more additional input medical images based on the propagated regions of interest and the set of candidate masks;
performing one or more assessments of the lesion based on the mask for the initial input medical image, the masks for the one or more additional input medical images, and prior assessments of lesions; and
outputting results of the one or more assessments of the lesion.

16. The non-transitory computer readable medium of claim 15, wherein curating a mask of the lesion for the initial input medical image based on the region of interest and a set of candidate masks comprises:
comparing the lesion with each candidate mask in the set of candidate masks; and
selecting a candidate mask from the set of candidate masks as the mask of the lesion based on the comparing.

17. The non-transitory computer readable medium of claim 15, wherein performing one or more assessments of the lesion based on the mask for the initial input medical image, the masks for the one or more additional input medical images, and prior assessments of lesions comprises:
characterizing the lesion across sequences, phases, and time points of the plurality of input medical images.

18. The non-transitory computer readable medium of claim 15, the operations further comprising:
receiving a plurality of medical images of one or more lesions;
identifying a modality, a sequence, a phase, and a time point associated with each of the plurality of medical images;
segmenting anatomical objects of interest from each of the plurality of medical images based on the modalities, the sequences, the phases, and the time points;
segmenting the one or more lesions from each of the plurality of medical images based on the modalities, the sequences, the phases, and the time points to generate the set of candidate masks;

registering certain medical images from the plurality of images to generate the prior registration transformations; and performing one or more assessments of the one or more lesions based on the segmented anatomical objects of interest, the segmented one or more lesions, and the prior registration transformations to generate the prior assessments of lesions.

19. The non-transitory computer readable medium of claim 15, wherein the initial input medical image is an image of the plurality of input medical images acquired at a first time point and the one or more additional medical images are images of the plurality of input medical images acquired at subsequent time points.

20. The non-transitory computer readable medium of claim 15, wherein the plurality of input medical images comprises images acquired for different sequences and contrast phases.

* * * * *